United States Patent [19]

Fleck, Sr. et al.

[11] Patent Number: 5,481,904

[45] Date of Patent: Jan. 9, 1996

[54] OIL SPILLAGE DETECTOR

[75] Inventors: Charles J. Fleck, Sr., National Park; Charles J. Fleck, Jr., Sicklerville, both of N.J.; Michael J. Sweeney, Glenolden, Pa.

[73] Assignee: The United States of America as represented by the Secretary of the Navy, Washington, D.C.

[21] Appl. No.: 313,958

[22] Filed: Sep. 28, 1994

[51] Int. Cl.[6] ............................. G01N 33/26; G01N 1/20; G08B 17/10; G08B 25/10
[52] U.S. Cl. ........................ 73/61.51; 340/605; 340/632
[58] Field of Search ........................ 73/61.51; 340/632, 340/605; 210/96.1

[56] References Cited

U.S. PATENT DOCUMENTS

| | | | |
|---|---|---|---|
| 3,719,936 | 3/1973 | Daniels et al. | 340/605 |
| 4,237,721 | 12/1980 | Dolan | 73/31.05 |
| 4,351,642 | 9/1982 | Bonavent et al. | 340/605 |
| 4,446,370 | 5/1984 | Gergely | 250/301 |
| 4,549,171 | 10/1985 | Akiba et al. | 340/605 |
| 4,563,674 | 1/1986 | Kobayashi | 340/620 |
| 4,622,557 | 11/1986 | Westerfield | 342/357 |
| 4,827,246 | 5/1989 | Dolan et al. | 340/605 |
| 4,882,499 | 11/1989 | Luukkala et al. | 250/577 |
| 4,925,726 | 6/1990 | Buro et al. | 73/61.51 |
| 5,202,829 | 4/1993 | Geier | 364/449 |
| 5,208,465 | 5/1993 | Jacobson | 250/573 |
| 5,264,368 | 11/1993 | Clarke et al. | 340/605 |
| 5,319,376 | 6/1994 | Einger | 342/357 |
| 5,331,845 | 7/1994 | Bals et al. | 73/19.1 |
| 5,344,105 | 9/1994 | Youhanaie | 244/3.14 |

OTHER PUBLICATIONS

Advertisement (1. p.), catalog information (10 pp.) and other product information (20 pp.) for Figaro gas sensors, Figaro USA, Inc., 1000 Skokie Blvd., Ste. 575, Wilmette, Ill. 60091

*Primary Examiner*—Hezron E. Williams
*Assistant Examiner*—Daniel S. Larkin
*Attorney, Agent, or Firm*—Howard Kaiser

[57] ABSTRACT

An oil spill sensing/communicating apparatus which is buoyantly situated, anchored or adrift, in a salt or fresh body of water, featuring a configuration which permits fluid passage therethrough of surface water/oil and sensing of hydrocarbonous gas which is emitted/exhaled from the oil. The apparatus thus functions effectively regardless of visual conditions because it "smells" rather than "sees" the oil which is present. Oil detection is signaled by the apparatus via light transmission and/or via radio transmission of location coordinates; some adrift embodiments use the Global Positioning System of satellite communication for continually updating the radio-transmitted location coordinates.

20 Claims, 4 Drawing Sheets

OIL SPILLAGE DETECTOR

The invention described herein may be manufactured and used by or for the Government of the United States of America for governmental purposes without the payment of any royalties thereon or therefor.

BACKGROUND OF THE INVENTION

The present invention relates to an apparatus and a method for detecting the presence of a substance or substances in or on a medium, more particularly to such apparatus and method wherein the substance or substances are hydrocarbonous (especially, petrochemical) in nature and the medium is water.

In recent times various forms of air and water pollution have damaged or threatened our world's environment and its lifeforms. Preservation of the earth's environment has become a major concern to its inhabitants.

Petrochemical (often referred to as "oil") spillage from off-shore drilling platforms, tankers and pipelines constitutes a rampant and insidious form of water pollution. Among the various approaches to monitoring oil spillage, perhaps the least efficient are those requiring direct human sensory (e.g., visual or olfactory) perception of the waters from land sites, aircraft or marine craft. Potentially more efficient is an approach which, rather than rely on human senses, automatically senses and signals the presence of hydrocarbonous matter in a given body of water.

Utilization of fiber optic technology for automatically detecting oil spillage is disclosed by Jacobson U.S. Pat. No. 5,208,465 and Luukkala et al. U.S. Pat. No. 4,882,499. Gergely U.S. Pat. No. 4,446,370 discloses automatic light detection of induced fluorescence in oil. These and other oil detection methodologies which analogously rely upon direct visual observation/sensing of the oil are rendered ineffective or less effective, however, in situations wherein the oil sought to be perceived does not appreciably deviate in appearance or color from that of the ambient water.

Hence, oil spillage detection approaches which are based on ocular principles may be limited or compromised by lack of visibility of the oil, for example due to darkness of night or to "blending in" of the oil with the surrounding water. On the other hand, as anyone having a normal sense of smell can attest, a hydrocarbonous liquid substance virtually always emits or evaporates a discernible hydrocarbonous gaseous substance, regardless of the visual circumstances.

SUMMARY OF THE INVENTION

In view of the foregoing, it is an object of the present invention to provide an oil spillage detector which is buoyantly situated in a body of water and which efficiently and reliably senses the presence of hydrocarbonous matter at or near the surface of the water.

It is a further object of the present invention to provide such an oil spillage detector which functions effectively under all conditions of visibility.

Another object of this invention is to provide such an oil spillage detector which functions effectively regardless of the appearance or coloration of the hydrocarbonous matter.

The present invention provides apparatus for discerning the presence of hydrocarbonous matter at or near the surface of an aqueous/hydrous liquid, the hydrocarbonous matter including a hydrocarboneous gaseous substance. The apparatus comprises a buoyant object having means for fluidly capturing portions of the aqueous/hydrous liquid and of the hydrocarbonous matter, and means for detecting some of the hydrocarboneous gaseous substance which is given off from at least one of the fluidly captured portions. For preferred embodiments the apparatus further comprises means for communicating the detecting of some hydrocarboneous gaseous substance.

The present invention also provides a method for discerning the presence of hydrocarbonous matter at or near the surface of an aqueous/hydrous liquid, the hydrocarbonous matter including a hydrocarboneous gaseous substance. The method comprises fluidly capturing portions of the hydrous liquid and of the hydrocarbonous matter, and detecting some of the hydrocarboneous gaseous substance which is given off from at least one of the fluidly captured portions. For preferred embodiments the method further comprises communicating the detecting of some hydrocarboneous gaseous substance.

"Oil" or "petrochemical," as used herein, refers to any of multifarious forms of "hydrocarbonous" matter (i.e., hydrocarbon-containing matter), especially such as includes or derives from petroleum or natural gas. "Water," as used herein, refers to any of multifarious forms of "aqueous/hydrous" liquid (i.e., water-like, water-derived, water-based or water-containing liquid), especially such as is found in an ocean, sea, gulf, bay, lake, river, stream, channel, strait, harbor or other "body of water."

By configurationally allowing fluid capture of surface matter and incorporating known technology in the hydrocarbonous gas sensing art (See, e.g., The Manual of Classification of the U.S. Patent and Trademark Office, Class 340, Subclass 632.), the hydrocarbon detection apparatus and method of the present invention singularly feature "smelling," rather than "seeing," of the hydrocarbonous matter which is located at or near the water surface. The oil detection system of this invention thus advantageously succeeds where visually dependent oil detection systems fail.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described by way of example, with reference to the accompanying drawings, wherein like numbers indicate the same or similar components, and wherein.

DETAILED DESCRIPTION OF THE INVENTION

Figure 1:
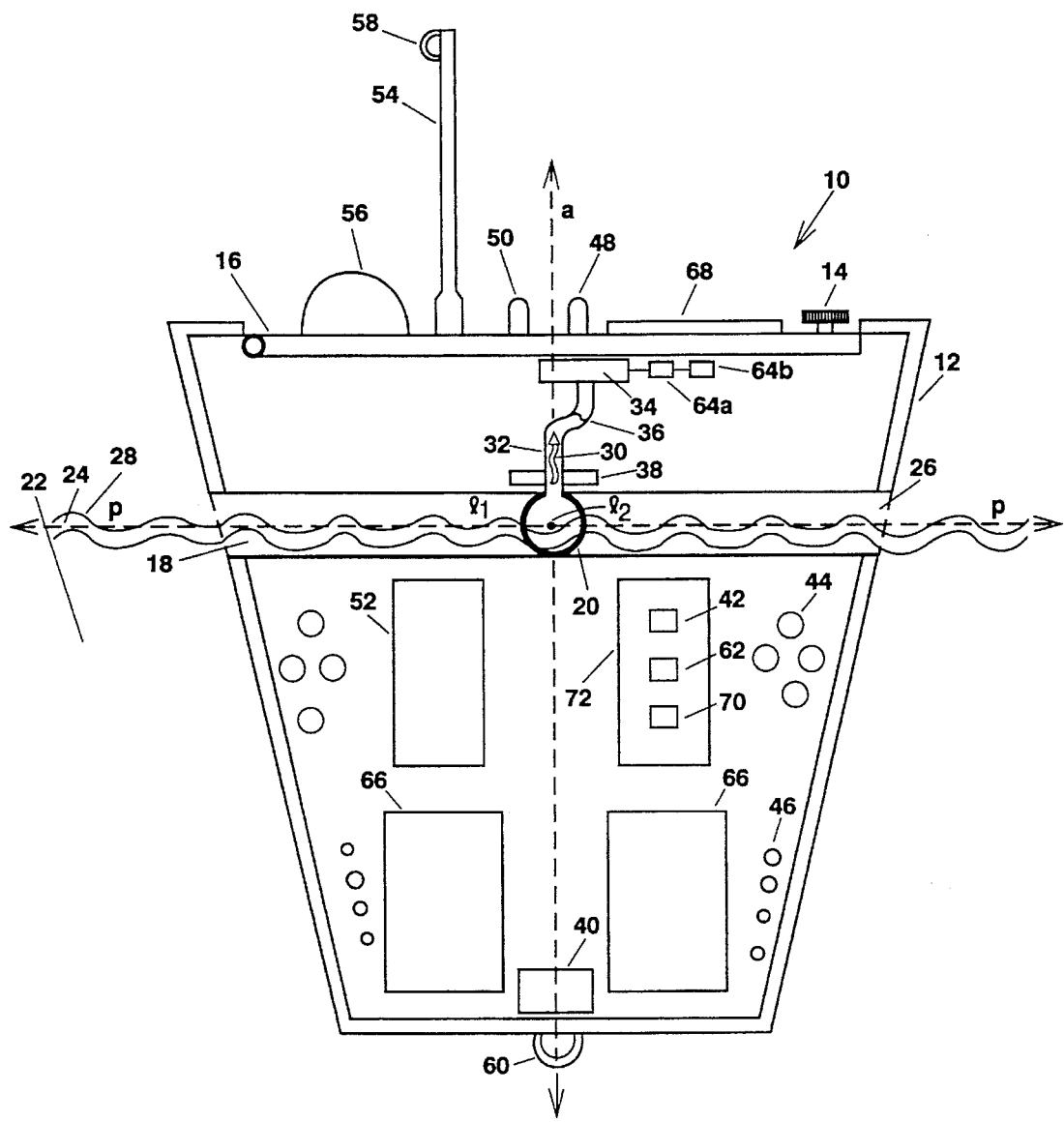
FIG. 1 is a diagrammatic elevation view of an embodiment of the apparatus in accordance with the present invention, with portions cut away to reveal interior details.
Figure 2:
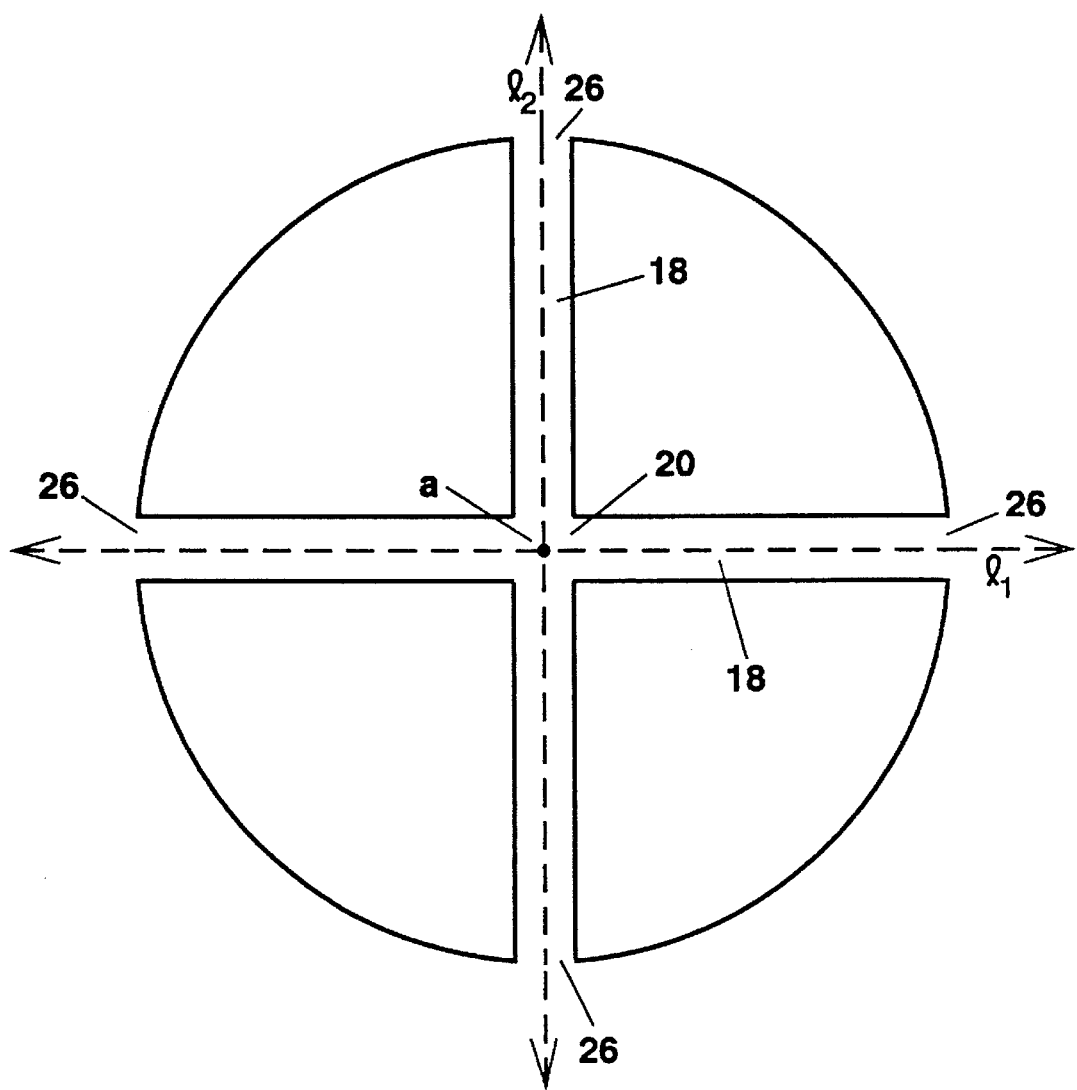
FIG. 2 is a diagrammatic plan view of the embodiment shown in FIG. 1, with portions cut away to reveal interior details.

Referring now to FIG. 1 and FIG. 2, oil spilage sensor/communicator unit 10 includes buoyant object 12, which houses unit 10. Buoyant object 12 in this example is a molded, hollow bucket-like structure having watertight seals 14 and hinged door 16.

Buoyant object 12 has two tubes 18 which perpendicularly lie in an approximately horizontal plane. Tubes 18 are also each perpendicular with respect to central vertical axis a through buoyant object 12. The first tube 18 and the second tube 18 unobstructedly intersect at central space 20. Central vertical axis a is represented in FIG. 1 as imaginary dashed line a and in FIG. 2 as imaginary point a at the center of central space 20. FIG. 1 affords a longitudinal view of the first tube 18 and an axial view of the second tube 18.

Each tube 18 is a hollow, fluid-tight cylindrical passage which permits water 22 and oil 24 to fluidly enter and exit ports 26 while flowing through tube 18. This fluid motion of water 22 and oil 24 into, out of and through tube 18 is caused by the rocking motion of buoyant object 12 while floating in a body of water 22 wherein oil 24 buoyantly exists at or near water level 28.

Hydrocarboneous gaseous emissions/exhalations 30 from oil 24 which are present at or in the vicinity of central space 20 rise through conduit 32 and are sensed ("sniffed") by gas sensor 34. Preliminary testing of the present invention was performed by the U.S. Navy using gas sensors 34 which are available from Figaro USA, Inc., 1000 Skokie Blvd., Ste. 575, Wilmette, Ill., 60091.

Gas sensor 34 used by the U.S. Navy was Figaro model TGS822. Figaro model TGS822 is a high-sensitivity gas sensor, solid-state (and thus having greater life expectancy), operable at virtually all temperatures; it has flame-arrestor screening and a sensing element containing an internal heater. The internal heater advantageously serves to facilitate upward conduction of gaseous emissions/exhalations 30 through conduit 32 and is thus a preferred feature of the gas sensor or gas sensors used for practicing many embodiments of this invention. Figaro model TGS823 has a ceramic base which is more resistant to severe environments. These and other Figaro models (e.g., Figaro model TGS 813) manufactured by Figaro offer similar features for various purposes and one or more models may be suitable or preferable for a particular embodiment or application of the present invention. In practicing this invention the making of gas sensor 34, or selection of gas sensor 34 from Figaro or another manufacturer, is well within the scope of ordinary skill in the art.

Check valve 36 (for example, a flapper valve) allows continued ascension of gaseous matter through conduit 32 while stopping ascension of liquid matter therethrough; thus, gaseous emissions/exhalations 30 are allowed to go on to reach gas sensor 34 while liquid matter from water 22 and oil 24 is prevented from reaching gas sensor 34.

For some embodiments and especially for embodiments of the present invention wherein gas sensor 34 lacks internal heating means, external heating means is preferably provided, such as by heater 38 shown in FIG. 1 in this example. Heater 38 serves to facilitate (or further facilitate, when gas sensor 34 has internal heating means), in a manner akin to a chimney or flue, upward conduction by conduit 32 of gaseous emissions/exhalations 30.

Compact, automatic bilge pump 40 is provided, according to some embodiments of the invention, for removing liquid which collects in the lower interior areas of buoyant object 12; an electronic chip, bilge chip 42, senses the liquid and actuates bilge pump 40 when the liquid reaches a predetermined height or quantity with respect to the interior of buoyant object 12.

For other embodiments sealed reserve flotation 44 is provided in lieu of or in addition to bilge pump 40 for preventing sinking of buoyant object 12. Reserve flotation 44 can include, for example, ping pong balls and/or light polystyrene (e.g., styrofoam) material. Reserve flotation 44 is preferably removable when unit 10 requires maintenance or repair.

Ballast 46, for enhancing stability and maintaining desired water level 28 in relation to buoyant object 12, is preferably adjustable in accordance with the characteristics (e.g., salt water versus fresh water) of water 22.

It is important for appropriate functioning of most embodiments of the apparatus in accordance with the present invention that stability and buoyant height of buoyant object 12 be suitably maintained during flotation, so that portions of the surrounding medium are fluidly captured by buoyant object 12 on a fairly continuous basis, the apparatus thus more efficiently effectuating its purpose of monitoring water 22 for presence of hydrocarbonous matter.

Hence, it is preferable that, during flotation of buoyant object 12, the cylindrical center lines 1 of tubes 18 generally lie in horizontal plane p, which is approximately coplanar with water level 28. The cylindrical center lines 1 for first tube 18 and second tube 18 in this example are represented in FIG. 1 as imaginary dashed line $1_1$ and imaginary point $1_2$, respectively, and are represented in FIG. 2 as imaginary dashed line $1_1$ and imaginary dashed line $1_2$, respectively. Horizontal plane p is represented in FIG. 1 as imaginary dashed line p which is colinear with imaginary dashed line $1_1$. Cylindrical center lines $1_1$ and $1_2$ are generally sustained in horizontal plane p, thereby permitting fluid movement of the surrounding medium into/out of ports 26 and within/without tubes 18.

Some embodiments preferably provide exterior indication or indicia as to the height to which water level 28 should rise on the apparatus. Accordingly, buoyant object 12 preferably has painted or otherwise indicated exteriorly thereon a desired water line, which also may be considered as illustrated by imaginary dashed line $1_1$ in FIG. 1, the desired water line thus being about even with cylindrical center lines $1_1$ and $1_2$ and with horizontal plane p.

It is important for most embodiments that buoyant object 12 be seen during nighttime and other periods of lesser visibility. Unit 10 in this example is provided with an occulating yellow light, navigation light 48, especially valuable as a nighttime warning/locator.

Sensing of gaseous emissions/exhalations 30 by unit 10 is preferably signaled; detection communication is accomplished by any of several ways, preferences depending on the embodiments of the invention. Some embodiments may provide visual indication of oil spill detection such as by a flashing red light, detection signal light 50, which is provided for unit 10.

Many embodiments of the present invention preferably provide radio communication as alternative to or, more preferably, in addition to a visual signal such as detection signal light 50. The radio communication can be voice or code. Gas sensor 34 may be thus mated with any of various devices in order that oil spillage sensor/communicator unit 10 perform various missions or meet various requirements. The unit 10 embodiment shown in FIG. 1 is provided with RF (radio frequency) transmitter 52, aerial 54 and GPS (Global Positioning System) receiver/dome 56.

The present invention contemplates both "anchored" and "adrift" modes of placement/deployment of the apparatus, preferably for extended periods of time, in accordance with and depending upon its various embodiments and applications.

For some anchored embodiments gas sensor 34 is mated with electronics which include RF transmitter 52 and aerial 54. For some adrift embodiments gas sensor 34 is mated with electronics which include RF transmitter 52, aerial 54 and GPS receiver/dome 56. In order to facilitate placeability or maneuverability of unit 10 for some embodiments it may conveniently be provided with positioning/retrieval hook 58 which is attached or configured at or toward the upper end of aerial 54 as shown in FIG. 1.

With regard to anchored embodiments, for some such embodiments at least one unit 10 may be deployed in an anchored position in body of water 22, e.g., a river, bay or channel. Once a unit 10 is anchored in place, for example using anchor hook 60 attached at the bottom of buoyant object 12, the GPS coordinates of that unit 10 are spoken into a memory which is capable of storing speech for transmittal, such as is found in digital telephone answering machine technology.

When a particular unit 10 senses oil 24, RF transmitter 52 for that unit 10 is activated and broadcasts to the cognizant parties the voice message from memory that oil 24 is present at or near the surface (i.e., water level 28) of body of water 22 at the GPS coordinates which have been spoken into memory for that unit 10; for most of these embodiments unit 10 preferably incorporates an internal clock/calendar (time/day or time/date), as in known telephone answering machine technology, so as to include in the broadcast voice message, in addition to the recorded message as to detection of the oil 24 slick at the fixed location of the unit 10, the time and date that the oil 24 slick was first detected.

Figure 3:
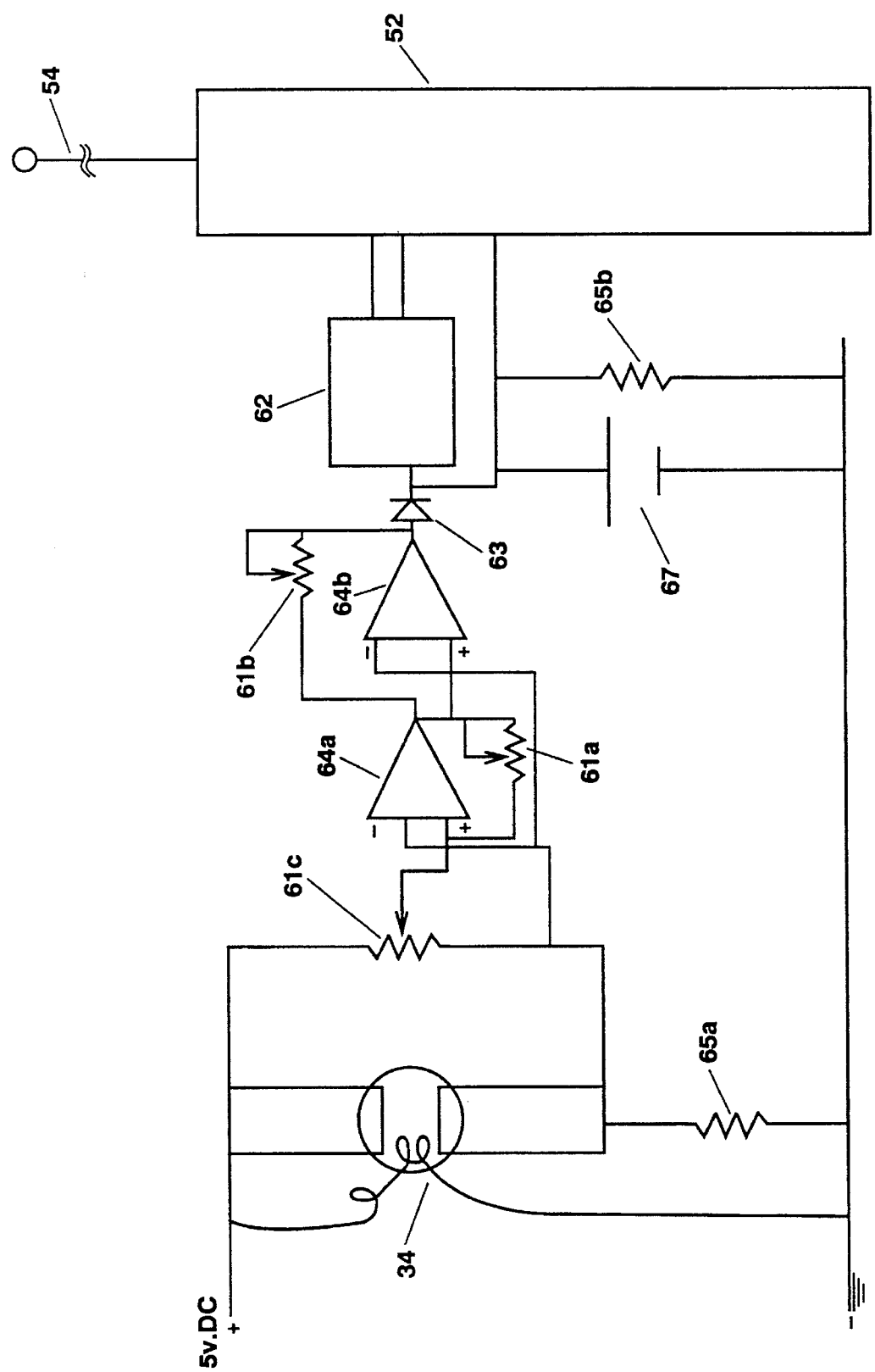
FIG. 3 is a schematic electronic diagram for an anchored embodiment of the apparatus in accordance with the present invention.

With reference to FIG. 3, a radio microphone has been used to record a message (the GPS coordinates for unit 10) on voice chip 62. Electronic gas sensor 34, upon sensing gaseous emissions/exhalations 30, sends a signal which is amplified by amplifiers 64a and 64b (also indicated in FIG. 1) and which activates RF transmitter 52 which transmits via aerial 54 the recorded message.

Some anchored embodiments take an alternative approach of providing each unit 10 with self-anchoring means (e.g., one or more propellers or water jets or other means of self-propulsion) and strategically deploying a plurality of units 10 with regard to an oil spillage event which has taken place. For example, units 10 may be deployed from a helicopter or boat in ever-widening circles around a ship which is leaking oil 24, for example due to a collision or due to having run aground. The size and progression of an oil 24 slick may thus be systematically determined using the GPS coordinates which have been spoken into memory at the time of deployment for each of a number of units 10 and which are broadcasting from particular units 10 at their corresponding times and locations as a consequence of their sensing of gaseous emissions/exhalations 30.

The ability of the present invention to operate even in the absence of light thus provides advantage which is especially manifest when tracking progressions of oil slicks. With regard to adrift embodiments of this invention, oil slick progressions may also be effectively tracked by placing a plurality of units 10 into water 22 at the location of an oil 24 slick and allowing each unit 10 to drift with the oil 24. Inasmuch as the "sail area" of unit 10 is small the likelihood of its drifting away from the oil 24 is minimal.

According to some adrift embodiments, the location of unit 10 is continuously kept current using known GPS technology such as is utilized by the "Slik-trak GPS" tracking buoy, available from Trimble Navigation, 645 North Mary Avenue, P.O. Box 3642, Sunnyvale, Calif., 94088-3642. The "Slik-trak GPS" tracking buoy implements a satellite-aided system whereby the buoy's precise location in real time is reported, twenty-four hours a day; the buoy's longitude and latitude data are transmitted by the buoy's internal radio modem to a computer equipped with appropriate tracking software.

Figure 4:
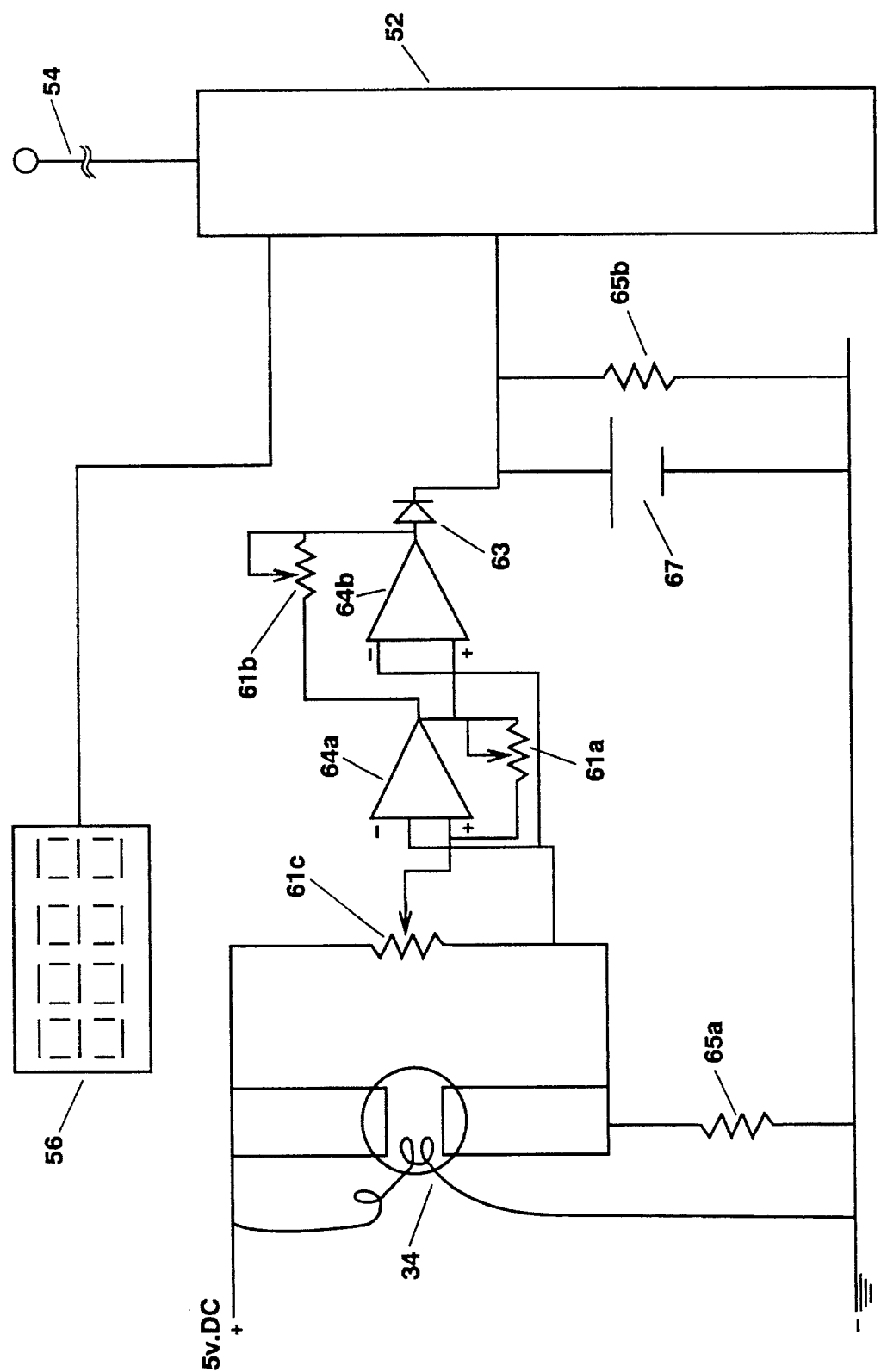
FIG. 4 is a schematic electronic diagram for an adrift embodiment of the apparatus in accordance with the present invention.

Referring to FIG. 4, GPS receiver/dome 56 engages RF transmitter 52. On a continuous basis, GPS receiver/dome 56 digitizes GPS coordinate information newly received from a satellite and sends it through a NEMA (National Electrical Manufacturers Association) plug to RF transmitter 52. Electronic gas sensor 34, upon sensing gaseous emissions/exhalations 30, sends a signal which is amplified by amplifiers 64a and 64b and which activates RF transmitter 52. However, instead of transmitting via aerial 54 a voice message which recites a recorded fixed location as for anchored embodiments (as well as time/day or time/date for some anchored embodiments), RF transmitter 52 transmits via aerial 54 the current GPS digital code. The cognizant parties (e.g., on a base, coast guard station, marine craft or aircraft) use a computer to decode or process the GPS code information which has been radio-transmitted by RF transmitter 52. Some embodiments preferably adopt regular radio-transmittal as standard procedure, e.g., whereby unit 10 periodically (e.g., every three hours) "identifies" itself and provides a current locational status for the cognizant parties.

For most embodiments of the present invention a d.c. power supply, for example, batteries 66 shown in FIG. 1, powers the electronics for the apparatus. An embodiment made and tested by the U.S. Navy utilized two 12 volt, 10 amp-hour rechargeable batteries 66. Rather than require periodic recharging of batteries 66, it is preferred that a constant charge for batteries 66 be maintained by solar cells 68 using known technology such as is found in pocket calculators. It is preferable for some embodiments that the stationed cognizant parties be afforded remote "shutdown" means for inactivating unit 10 so as to save power during periods of dormancy.

In this example, still referring to FIG. 1, the electronics for unit 10 include gas sensor 34, bilge pump 40, bilge chip 42, navigation light 48, detection signal light 50, RF transmitter 52, aerial 54, GPS receiver/dome 56, voice chip 62, amplifiers 64, communication coordination chip 70, electronics package 72 and appropriate wiring (not shown). Electronics package 72 houses bilge chip 42, voice recording chip 62, communication coordination chip 70 and pertinent circuitry. Communication coordination chip 70 programs noninterference among a group of units 10 when sending radio transmissions.

Referring again to FIG. 3 and FIG. 4, an embodiment of the present invention which was made and tested by the U.S. Navy utilized six inch aerial 54; 1 meg. ohms adjustable potentiometers 61a and 61b and 5 K. ohms adjustable potentiometer 61c; general purpose diode 63; no. 741 operational amplifier 64a; no. CA4130 operational amplifier 64b; 2.4 K. ohms, ½ watt resistor 65a; 10 meg. ohms resistor 65b; 1.0 MFD, 12 volt capacitor 67.

The fluid passage means in this example includes two "closed" channels 18 which are tubular or cylindrical in shape and hence referred to as tubes 18. According to varying embodiments of unit 10, the fluid passage means can include one or more closed channels 18 which are hollow conveyance members of tubular/cylindrical, rectangular or any other appropriate shape.

Any number of closed channels 18 can be utilized as fluid passages in accordance with the present invention. Referring again to FIG. 2, varying embodiments of unit 10 can be visualized as having varying numbers of tube 18 half-lengths which unobstructably meet like radii at central space 20 in varying configurations resembling spokes of a hub and wheel, one configuration of which is actually shown.

FIG. 1 and FIG. 2 illustrate approximate symmetry of two tubes 18 which are perpendicularly intersecting unobstructably at central space 20 as well as of buoyant object 12 circularly about central vertical axis a through the center of central space 20. A prototype embodiment of the present invention which was made and preliminarily tested by the U.S. Navy utilized a bucket-like buoyant object 12 having an approximately twelve-inch upper diameter, an approximately 10.5 inch lower diameter, an approximately fourteen-inch height and two approximately one-inch diameter tubes 18 in the approximately symmetrical configuration described in this example. However, buoyant object 12 may be, depending on the embodiment, symmetrically or asymmetrically shaped, and one or more closed channels 18 may be, depending on the embodiment, symmetrically or asymmetrically disposed in relation to buoyant object 12.

For some embodiments the fluid passage means includes one or more "open" channels which are not hollowed out conveyance members but rather are conveyance gaps or spaces separating portions of unit 10. For some such embodiments, for example, an upper section of unit 10 is coupled with a lower section of unit 10; one or more gaps, partially bounded laterally or virtually unbounded laterally, together serve to substantially separate or virtually entirely separate the upper section from the lower section.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. Apparatus for discerning the presence of hydrocarbonous matter at or near the surface of an aqueous/hydrous substance, said hydrocarbonous matter including a hydrocarbonous liquid substance and a hydrocarboneous gaseous substance, said apparatus comprising:

a buoyant hollow cylindroid object;

at least two diametrical horizontal tubes, said horizontal tubes extending through said object and unobstructively intersecting so as to form a central spatial junction within said object, said horizontal tubes being for fluidly capturing, at said central spatial junction, portions of said aqueous/hydrous substance and of said hydrocarbonous liquid substance;

a sensor remotely situated above said central spatial junction, said sensor being for detecting some said hydrocarboneous gaseous substance which is given off from at least one of said fluidly captured portions; and conduction means between said central spatial junction and said sensor, said conduction means including a conduit, a valve and a heater;

said conduit being long and narrow, said valve being for checking conducting said aqueous/hydrous substance and said hydrocarbonous liquid substance, said heater being for promoting conducting of said hydrocarboneous gaseous substance by said conduit, said conduction means thereby being adapted to permit said hydrocarboneous gaseous substance to reach said sensor and to prevent said aqueous/hydrous substance and said hydrocarboneous liquid substance from reaching said sensor.

2. Apparatus for discerning the presence of hydrocarbonous matter as in claim 1, further comprising means for communicating said detecting of some said hydrocarboneous gaseous substance.

3. Apparatus for discerning the presence of hydrocarbonous matter as in claim 1, further comprising adjustable ballast means within said object for enhancing the stability of said object and for maintaining the appropriate level of said surface in relation to said object.

4. Apparatus for discerning the presence of hydrocarbonous matter as in claim 1, further comprising a bilge pump for removing said aqueous/hydrous substance and said hydrocarbonous liquid substance which accumulate in lower interior regions of said object.

5. Apparatus for discerning the presence of hydrocarbonous matter as in claim 1, further comprising reserve flotation members within said object for preventing sinking of said object.

6. Apparatus for discerning the presence of hydrocarbonous matter as in claim 1, further comprising:

adjustable ballast means within said object for enhancing the stability of said object and for maintaining the appropriate level of said surface in relation to said object;

a bilge pump for removing said aqueous/hydrous substance and said hydrocarbonous liquid substance which accumulate in lower interior regions of said object; and reserve flotation members within said object for preventing sinking of said object.

7. Apparatus for detecting hydrocarbonous matter located at or near the surface of a body of water, said hydrocarbonous matter including a hydrocarbonous liquid substance and a hydrocarboneous gaseous substance, said apparatus comprising:

a buoyant hollow cylindroid vessel;

a plurality of horizontal tubes extending through said vessel, said horizontal tubes permitting fluid passage of said water and of said hydrocarbonous matter, said horizontal tubes openly intersecting the vertical axis of symmetry of said vessel and forming a junctional space at said vertical axis in said vessel;

a sensor for sensing the presence of said hydrocarboneous gaseous substance, said sensor distanced above said horizontal tubes in said vessel;

a conduit substantially aligned with said vertical axis, said conduit coupling said sensor with said junctional space, said conduit having such dimensions and configuration as to be disposed to permitting conduction of said hydrocarboneous gaseous substance to the vicinity of said sensor and indisposed to permitting conduction of said water and said hydrocarboneous liquid substance to said vicinity;

a heater for facilitating said conduction of said hydrocarboneous gaseous substance by said conduit; and a valve for checking conduction of said water and said hydrocarboneous liquid substance by said conduit.

8. Apparatus for detecting hydrocarbonous matter as in claim 7, further comprising means for communicating said sensing of the presence of said hydrocarboneous gaseous substance.

9. Apparatus for detecting hydrocarbonous matter as in claim 8, wherein said means for communicating includes at least one light.

10. Apparatus for detecting hydrocarbonous matter as in claim 8, wherein said means for communicating includes radio communication means.

11. Apparatus for detecting hydrocarbonous matter as in claim 10, wherein said radio communication means includes radio frequency transmitting means.

12. Apparatus for detecting hydrocarbonous matter as in claim 10, wherein said radio communication means includes radio frequency transmitting means and Global Positioning System receiving means.

13. Apparatus for detecting hydrocarbonous matter as in claim 7, further comprising adjustable ballast means in said vessel for enhancing the stability of said vessel and for maintaining the appropriate level of said surface in relation to said vessel.

14. Apparatus for detecting hydrocarbonous matter as in claim 7, further comprising a bilge pump for removing said water and said hydrocarbonous liquid substance which collect in lower interior regions of said vessel.

15. Apparatus for detecting hydrocarbonous matter as in claim 7, further comprising reserve flotation members in said vessel for preventing sinking of said vessel.

16. Apparatus for detecting hydrocarbonous matter as in claim 7, further comprising:

adjustable ballast means in said vessel for enhancing the stability of said vessel and for maintaining the appropriate level of said surface in relation to said vessel;

a bilge pump for removing said water and said hydrocarbonous liquid substance which collect in lower interior regions of said object; and reserve flotation members in said vessel for preventing sinking of said vessel.

17. Method for discerning the presence of hydrocarbonous matter at or near the surface of an aqueous/hydrous substance, said hydrocarbonous matter including a hydrocarbonous liquid substance and a hydrocarboneous gaseous substance, said method comprising:

floating in said aqueous/hydrous substance a buoyant cylindroid unit which includes at least two diametrical horizontal tubes, a sensor, a conduit, a valve and a heater, said unit being adapted to permitting said hydrocarboneous gaseous substance to reach said sensor while preventing said aqueous/hydrous substance and said hydrocarboneous liquid substance from reaching said sensor, said tubes extending through said unit and unobstructively intersecting so as to form a central spatial junction within said unit, said sensor remotely situated above said central spatial junction, said conduit having appropriately narrow dimension, said valve checking the conducting of said aqueous/hydrous substance and said hydrocarbonous liquid substance, said heater promoting the conducting of said hydrocarboneous gaseous substance by said conduit;

fluidly capturing portions, at said central spatial junction, of said aqueous/hydrous substance and of said hydrocarbonous matter; and detecting, by means of said sensor, some said hydrocarboneous gaseous substance which is given off from at least one of said fluidly captured portions.

18. Method for discerning the presence of hydrocarbonous matter as in claim 17, further comprising communicating said detecting of some said hydrocarboneous gaseous substance.

19. Method for discerning the presence of hydrocarbonous matter as in claim 17, further comprising providing ballast for said unit and adjusting said ballast for enhancing the stability of said unit and for maintaining the appropriate level of said surface in relation to said unit.

20. Method for discerning the presence of hydrocarbonous matter as in claim 17, further comprising:

providing a bilge pump for said unit and using said bilge pump for removing said aqueous/hydrous substance and said hydrocarbonous liquid substance which accumulate in lower interior regions of said unit; and providing reserve flotation members in said unit for preventing sinking of said unit.

* * * * *